United States Patent [19]

Hutchison et al.

[11] 4,064,735
[45] Dec. 27, 1977

[54] EXCITATION AND SPECTRAL CALIBRATION OF ACOUSTIC EMISSION SYSTEMS

[75] Inventors: Thomas Sherret Hutchison, Kingston; Stuart Livingstone McBride, Invarerary, both of Canada

[73] Assignee: Her Majesty the Queen in Right of Canada, as represented by the Minister of National Defence, Ottawa, Canada

[21] Appl. No.: 707,181

[22] Filed: July 21, 1976

[30] Foreign Application Priority Data

Sept. 16, 1975 United Kingdom ............. 037909/75

[51] Int. Cl.² ........................................... G01C 25/00
[52] U.S. Cl. .................................... 73/1 R; 73/88 R
[58] Field of Search ............. 73/1 DV, 37, 70, 88 R, 73/556, 557, 558

[56] References Cited

U.S. PATENT DOCUMENTS

3,830,091  10/1974  Sinsky ................................. 73/1 DV

*Primary Examiner*—Jerry W. Myracle
*Attorney, Agent, or Firm*—Shanley, O'Neil and Baker

[57] ABSTRACT

A method and apparatus for the excitation and spectral calibration of acoustic emission systems in which a helium or other gas jet is used as a calibration source which makes no mechanical contact with the specimen or structure under examination. The gas jet which simulates an acoustic emission event, is sprayed on a reference material which is acoustically coupled to either an acoustic emission transducer or to a transducer having a flat frequency response up to 1 MHz. The transducer spectra are measured in decibels and subtracted from each other thereby obtaining a "transducer calibration". The "calibrated" transducers are then coupled to a specimen under test, the gas jet is applied and a "gas jet system spectrum" is measured. The spectrum of acoustic emission activity is then measured and corrected by subtracting, in decibels, the "gas jet system spectrum", thereby obtaining system independent acoustic emission spectral information which can be used to compare results in other systems.

15 Claims, 16 Drawing Figures

EXCITATION AND SPECTRAL CALIBRATION OF ACOUSTIC EMISSION SYSTEMS

This invention relates to a method and apparatus for the excitation and spectral calibration of acoustic emission systems.

Acoustic emissions, hereinafter referred to as A.E., are emissions having frequencies generally in the range 50KHz up to several megahertz which emanate from various physical phenomena within a material. A.E. sources include mechanical phase transitions, grain boundary motion, ductile, and brittle fracture, stress corrosion, and the like, in a large number of materials such as steels, aluminum alloys, titanium alloys, ceramics and composite materials.

If the source of the A.E. can be identified it follows that an assessment of the probable remaining life of a component and accurate prediction of failure in advance of a catastrophic failure system may be made by comparison of a test spectrum with laboratory standards. Heretofore it has been a standard technique to measure the output of a transducer at each of a number of different frequencies when the transducer is excited by a source of broad band radiation. One means for producing the broad band noise in current favour is known as the "spark bar technique". In this technique a shock surface wave is excited by an electrical spark discharge and propagated along a bar. The transducer under test is then applied to the same surface of the bar. As explained in more detail hereinafter, it can be shown quite readily that the current use of this calibration method pertains to the transducer only and does not take into account the vibration modes of the component or structure to which the transducer is attached.

It is believed, therefore, that a fundamentally different approach to spectral calibration of the system within which the A.E. source emits, is required. As used herein the term "system" is defined as the specimen or component containing the A.E. source, the couplant to the sensor, the sensor itself and the particular amplifying and recording electronic hardware employed. It is believed fundamental to the obtension of quantitative, as opposed to qualitative, spectral data of the A.E. source that the entire system shall be calibrated, and that the calibration technique be such that it provides system independent A.E. spectral data. This requires that (a) it provides transducer independent information for A.E. signals; (b) it is usable for laboratory calibration of transducers; (c) it is safe, portable and inexpensive and can be used to "calibrate" the entire test system in the laboratory or field; and (d) data can be transferred from one system (e.g. lab specimen) to another (e.g. field component) and proper data exchange can be made between laboratories.

It is one object of the present invention to provide a method for calibrating an acoustic emission system.

It is another object of the present invention to provide an apparatus for calibrating an acoustic emission system.

By one aspect of this invention there is provided a method for spectral calibration of acoustic emission systems, comprising:

a. acoustically coupling a first transducer, having a flat frequency response up to about 1 MHz, to a reference material;

b. exciting said reference material with a broad spectrum noise means, thereby generating an output signal from said first transducer;

c. measuring said output signal from said first transducer;

d. acoustically coupling a second transducer to a test piece and exciting said test piece with said broad spectrum noise means, thereby generating an output signal from said second transducer;

e. calibrating said output signal of said second transducer relative to said output signal of said first transducer;

f. measuring an acoustic emission spectrum from said test piece; and g. correcting said acoustic emission spectrum relative to said calibrated output signal of said second transducer.

By another aspect of this invention there is provided a method for calibrating a high frequency audio transducer comprising:

a. acoustically coupling said transducer to a reference material and exciting said material with a broad spectrum noise means, thereby generating an output signal from said transducer;

b. amplifying and analysing said output signal;

c. acoustically coupling a second transducer having a flat frequency response up to about 1 MHz to said reference material excited by said broad spectrum noise thereby generating a comparison output signal from said second transducer;

d. amplifying and analysing said comparison output signal; and e. calibrating said output signal against said comparison output signal.

By yet another aspect of this invention there is provided an apparatus for use in spectral calibration of acoustic emission systems comprising:

a reference material;

a test piece;

broad spectrum noise means to excite said reference material and said test piece;

transducer means for acoustic coupling to said test piece;

a comparison transducer having a flat frequency response up to about 1 MHz for acoustic coupling to said reference material; and means for recording and analysing output signals from said transducer means when coupled to said test piece and an output signal from said comparison transducer when coupled to said reference material whereby said output signals may be calibrated.

The invention will be described hereinafter with reference to the accompanying drawings in which.

Figure 1:
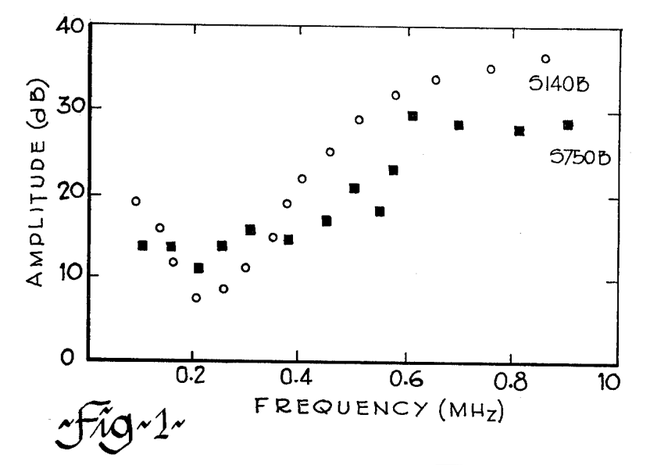
FIG. 1 is a graph showing frequency versus amplitude for two transducers calibrated according to the prior art.

Turning firstly to FIG. 1 which is illustrative of calibration according to the prior art spark-bar technique, two commercially available A.E. transducers, designated S140 and S750 by the manufacturers, Dunegan-Endevco Corporation of California, and having quite different characteristics, were connected to a specimen of 7075-T6 aluminum and were both used to simultaneously observe the same acoustic emission event induced in the specimen. After applying the supplied spark bar calibration to each transducer output, it was found, as illustrated in FIG. 1, that over the range of frequencies observed the derived spectra from the outputs of the two transducers differed by more than 10 dB, which is clearly insufficiently reliable for quantitative measurements.

Figure 2:
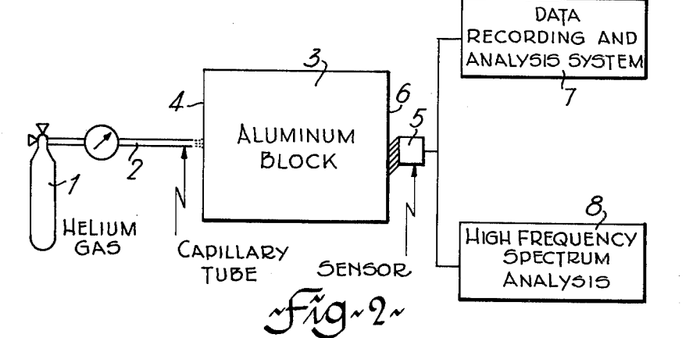
FIG. 2 is a schematic diagram of a portion of the apparatus according to the present invention.
Figure 3:
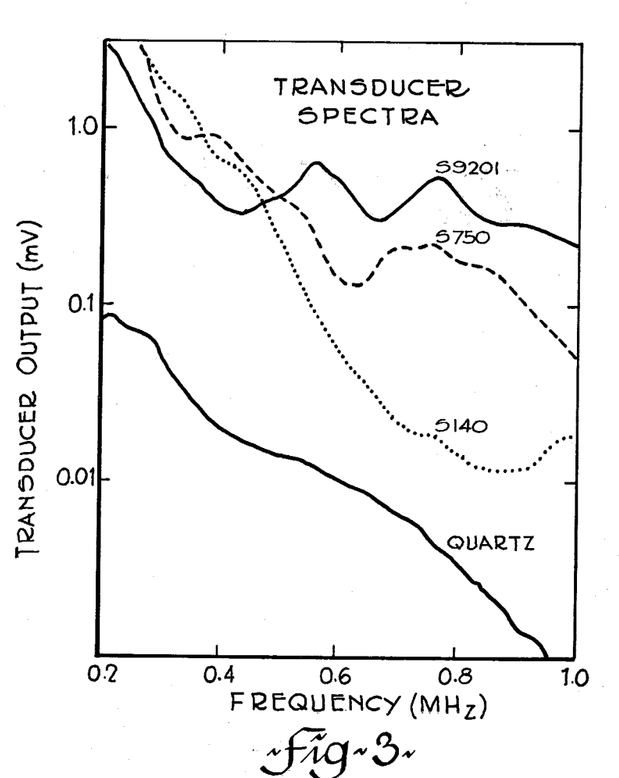
FIG. 3 is a graph of helium gas jet spectra of a 5MHz X-cut quartz crystal and commercial A.E. transducers coupled to an aluminum block.

In contrast to the prior art, FIG. 2 shows, in schematic form, an experimental layout for the spectral calibration of an A.E. system which can provide system independent A.E. spectral data. In preliminary experiments it was found that A.E. sensors were excited by blowing a gas through a narrow bore capillary tube onto a sensor face. Broad band noise, up to about 1 MHz, was obtainable using air, nitrogen, helium and other gases and mixtures thereof. As helium is a single atom, highly elastic and a light gas it has been found particularly suitable for the present purposes. It will also be appreciated that the parameters to achieve excitation depend upon the gas selected, the length and bore of the capillary tube and its spacing from the sensor face. For example, using helium gas data was obtainable up to 1 MHz at 18-40 psi, whereas using nitrogen data of a similar amplitude was obtainable at 80 psi. In FIG. 2, therefore, there is shown a helium gas source 1 and a capillary tube, 2, 0.8mm bore diameter and 6cm long, through which helium can be sprayed at a pressure of about 20 psi against a block of a reference material 3 placed about 1.8mm away. For convenience a 7075-T6 aluminum cylinder 4 inches long and 4.5 inches in diameter is used as the reference material. Noise generated, it is believed by the drumming of the helium gas on one face 4 of the cylinder, propagates through the cylinder and can be sensed by a transducer or sensor 5 acoustically coupled to the opposed face 6. The system is not, therefore, loaded by the activating noise source. Permanent recording and spectrum analysis of the sensor output can be obtained using a waveform recorder, such as a Biomation 805 waveform recorder, magnetic tape recorder 7, and a spectrum analyser 8, such as a Nelson-Ross spectrum analyser with 60 KHz resolution. It has been determined that a sensor which has a substantially frequency independent response up to about 1 MHz coupled to face 6 will yield the spectrum of the gas jet noise. A particularly suitable frequency independent sensor for use as a standard or, more accurately, as a sub-standard is an X-cut quartz crystal which has its fundamental mechanical resonance at about 5MHz, i.e. well above the frequency range of interest. A suitable sub-standard is a 0.25 inch diameter disc with a 0.125 inch diameter gold plated electrode and a wrap around gold plated ground shield as supplied by Valpe-Fisher Company of U.S.A. It will be appreciated, however, that any sensor which (a) has a flat frequency response up to 1 MHz and (b) is sensitive enough to determine the spectral character of the high amplitude gas jet noise, may be employed. The bottom curve in FIG. 3 shows the envelope of a 60 KHz resolution spectrum analysis of a helium gas jet signal measured using a Nelson-Rose spectrum analyser using the flat response quartz sensor, which is essentially the spectrum of the gas jet itself.

Figure 4:
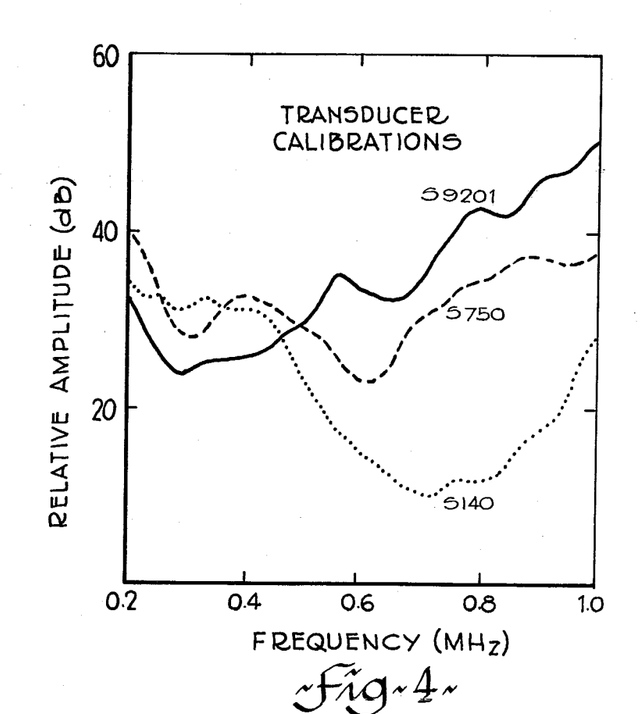
FIG. 4 is a graph showing calibration of the A.E. transducers, derived from the data of FIG. 3.

If the flat response quartz sensor on the block 3 is replaced by an A.E. transducer the response of the A.E. transducer to the same gas jet noise signal may be obtained. FIG. 3 also shows the measured spectrum of the aforesaid commercially available A.E. transducers S140 and S750, and also a similar A.E. transducer S9201. From the data presented in FIG. 3, transducer calibrations can be derived by comparing the amplitude ratios of the transducer output to that of quartz for each transducer at each frequency. This is most simply done by direct subtraction of the quartz spectrum, in decibels, from each transducer spectrum, in decibels, in turn. Without burdening the present specification with mathematical proofs, it will be appreciated that all output voltages are a function of frequency and hence directly related to amplitude. Transducer calibration can thus be defined as the output of the transducer relative to that of the flat response quartz sensor. Transducer calibrations for the three transducers referred to in FIG. 3 are shown in FIG. 4. Having thus determined the transducer calibration attention can be turned to calibration of an A.E. system. Attachment of the calibrated transducer to a test specimen or structure results in a system comprising transducer, couplant and specimen or structure, and it is the response of this system to A.E. activity which is to be determined. It is re-emphasized that calibration of the system is useful only if it can provide system independent information about the acoustic emission activity.

EXAMPLE 1

Helium gas jet calibration of an A.E. system.

Figure 5:
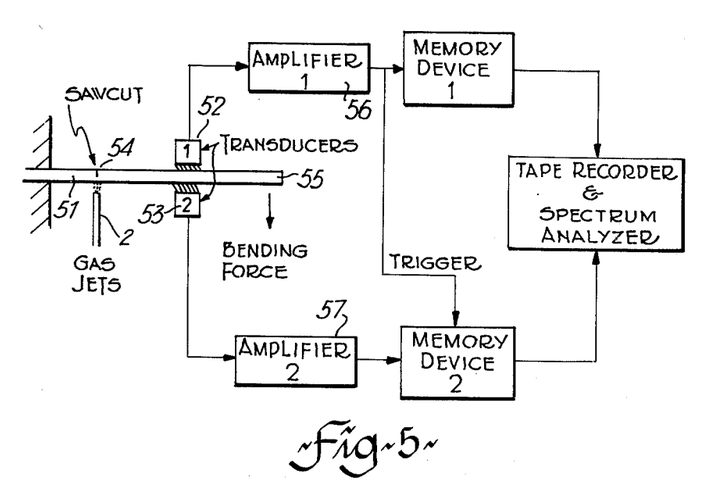
FIG. 5 is a schematic diagram of apparatus used in combination with the apparatus of FIG. 2 for illustrating simultaneous detection of an A.E. event by two systems to provide calibration of the systems and cross check the accuracy of calibration of two different transducers.
Figure 6:
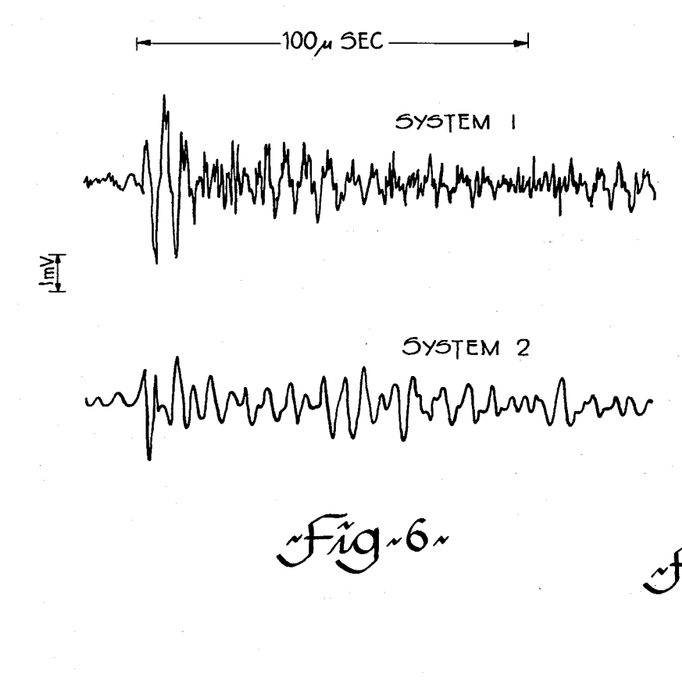
FIG. 6 is a trace of transducer output signals from an A.E. event recorded simultaneously on the two systems of FIG. 5.
Figure 7:
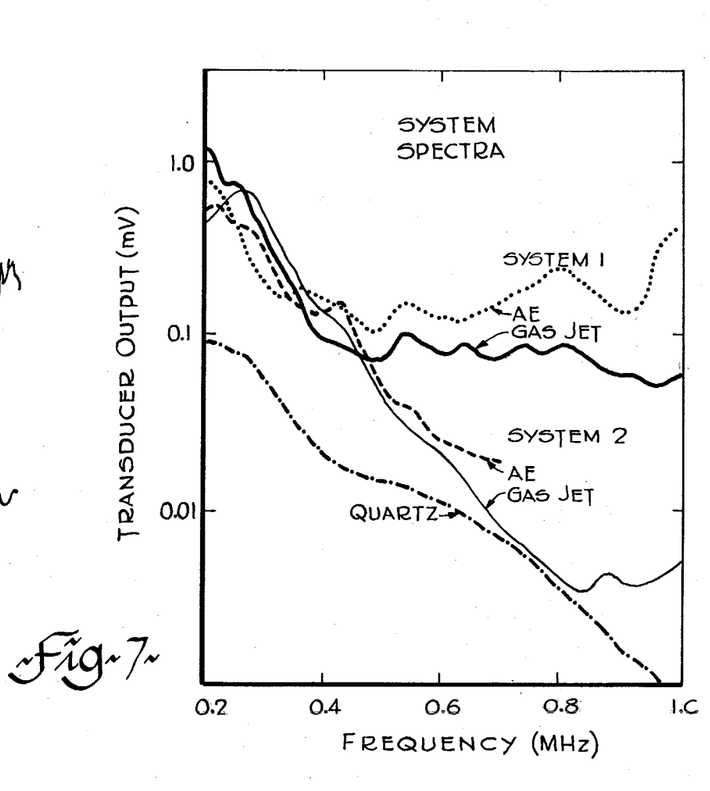
FIG. 7 is a graph of the spectra obtained by gas jet noise excitation of the systems of FIG. 5 and the first 50μ secs of the A.E. signals of FIG. 6. The gas jet noise spectrum of the quartz sensor attached to the aluminum block is shown for comparison.
Figure 8:
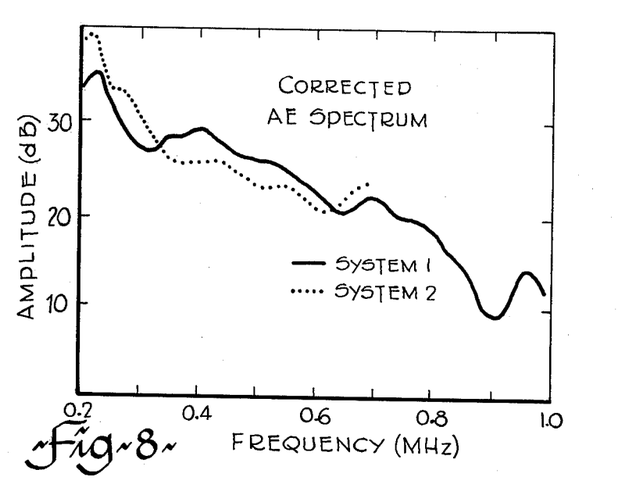
FIG. 8 is a graph showing corrected A.E. spectra for the systems of FIG. 5, obtained by eliminating the system behavior according to the present invention.

FIG. 5 illustrates an experimental layout for testing two systems employing distinctly different transducers which permits simultaneous detection of the same A.E. event by both systems and hence eliminates event differences. A 7075-T6 aluminum specimen 51 (12in. × 1 in. × 0.187 in.) was arranged as shown in FIG. 5. A pair of transducers 52 and 53 having quite different spectral responses were mounted 10 cm from a transverse saw cut 54. For convenience transducers 52 and 53 were the Dunegan-Endevco S140 and S9201 respectively whose gas jet transducer calibrations are shown in FIG. 4. A bending load at the end 55 produced A.E. activity in the vicinity of the saw cut 54. A 2-channel data collection system 56, 57 captured the same A.E. event as it was simultaneously sensed by each transducer. Gas jet noise from the helium gas jet 2 was injected into the specimen 51 below the saw cut 54 and the system output signals spectrum analysed. A.E. activity was then produced by increasing the bending load at 55 and an acoustic emission event simultaneously recorded from each transducer. The A.E. signals thus obtained are shown in FIG. 6. System 1 produced a broad band signal compared to that of system 2 which includes a transducer resonant at about 140 KHz. The system spectra for the gas jet noise signal and the simultaneously captured A.E. signals are shown in FIG. 7. From the gas jet data system calibrations were obtained, by decibel subtraction as described hereinabove, of the flat response quartz spectrum (FIG. 3) from the gas jet system spectra obtained using apparatus as shown in FIG. 5. The resulting system calibrations were then applied to the A.E. system spectra obtained using apparatus as shown in FIG. 2, again by decibel subtraction. The resulting corrected A.E. spectrum is shown for both systems in FIG. 8. It will be noted that the result is system independent to within 3dB for the dynamic range of the electronics (36 dB). This range applied to the A.E. signals. The resonant response of the S140 transducer was reduced, in a second experiment, by high pass filtering for the continuous gas jet measurement to extend the calibration to 1 MHz.

Figure 9:
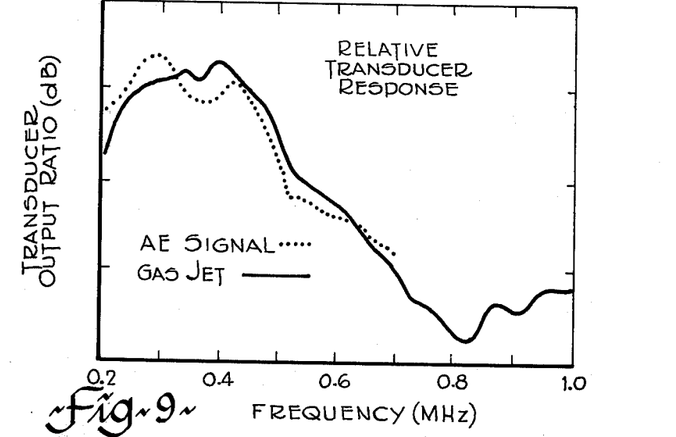
FIG. 9 is a graph showing comparison between the relative responses of the two systems of FIG. 5 to the helium gas jet noise signal and the simultaneously captured A.E. signal.

FIG. 9 shows the relative output of system 2 with respect to system 1 for both the gas jet and the A.E. event. The excellent agreement of the gas jet and A.E. responses shown in FIG. 9 along with the system independent spectra (FIG. 8) demonstrate the efficacy of the gas jet as an acoustic emission simulator, at least within a thin plate of 7075-T6 aluminum. Because A.E. events are known to be caused by highly localized material changes, i.e. much less than a wavelength for mechanical waves in the A.E. frequency range, it is believed that the simulation applies equally well to other materials provided the emitting source is sufficiently close to a surface accessible to the gas jet probe for calibration. With the information thus gathered along with background noise data and laboratory observations of A.E. can be used to evaluate material integrity, the probability of failure and the like in field situations.

EXAMPLE 2

Figure 10:
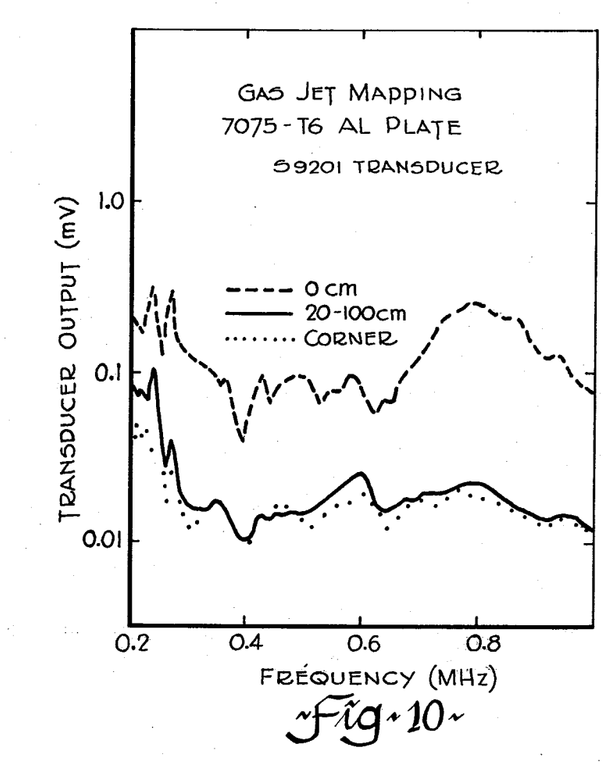
FIG. 10 is a graph showing gas jet mapping for a 7075-T6 aluminum plate using an S9201 transducer.
Figure 11:
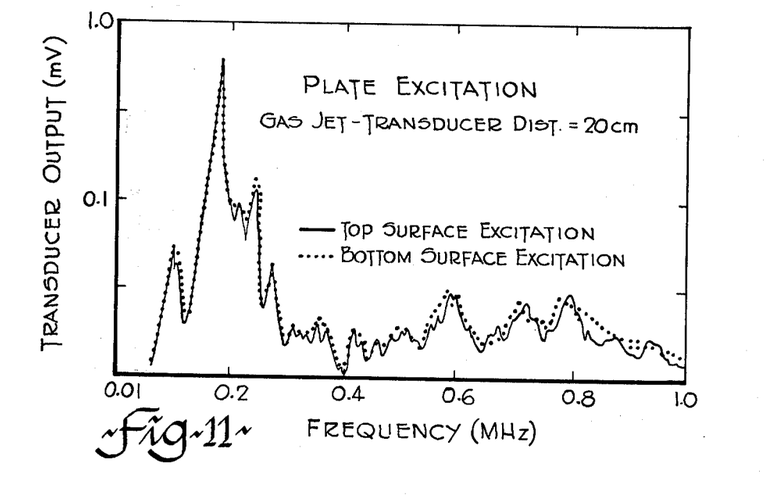
FIG. 11 is a graph, similar to FIG. 10, showing plate excitation at different locations.

In order to further demonstrate the use of the helium gas jet as an A.E. simulator, the procedures of Example 1 were repeated using a 3/16 inch thick 7075-T6 aluminum plate 6 feet long by 3 feet wide as the specimen. In this example an S9201 transducer was placed in the centre of one side of the plate and the gas jet signal was injected at each of three locations in turn: (a) directly aligned with the transducer on the opposite side of the plate (b) directly on the plate at distances between 20 and 100 cms. from the centre of the transducer on the top surface; and (c) in a corner of the plate. FIG. 10 shows that the position of the gas jet has little effect on the spectrum recorded. FIG. 11 shows the same experiments repeated with the gas jet spaced 20 cms. from the transducer applied firstly to the top surface and secondly to the bottom surface. Here again it is demonstrated that both surfaces are similarly excited, in a Lamb type rather than a Rayleigh type mode.

EXAMPLE 3

Figure 12:
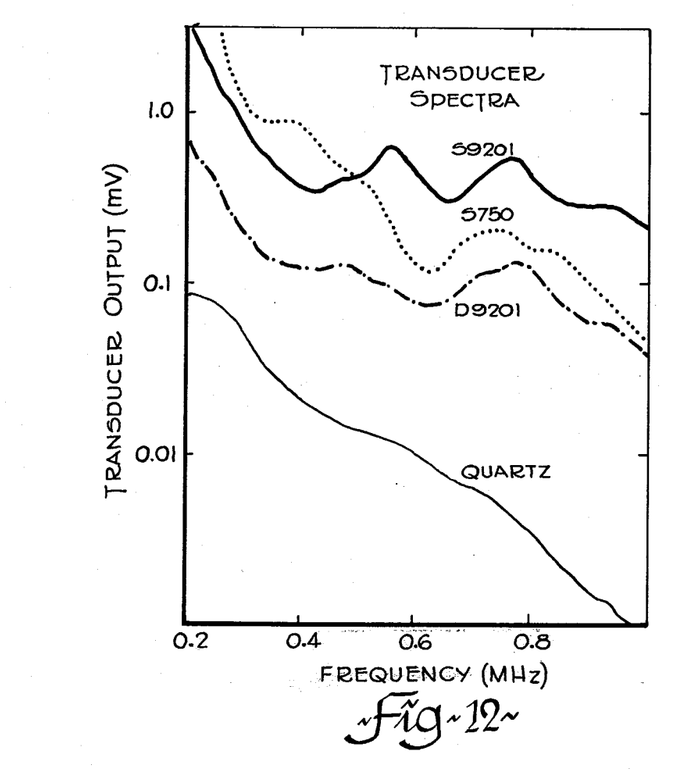
FIG. 12 is a graph showing transducer spectra for different A.E. transducers and compared to a flat response transducer.
Figure 13:
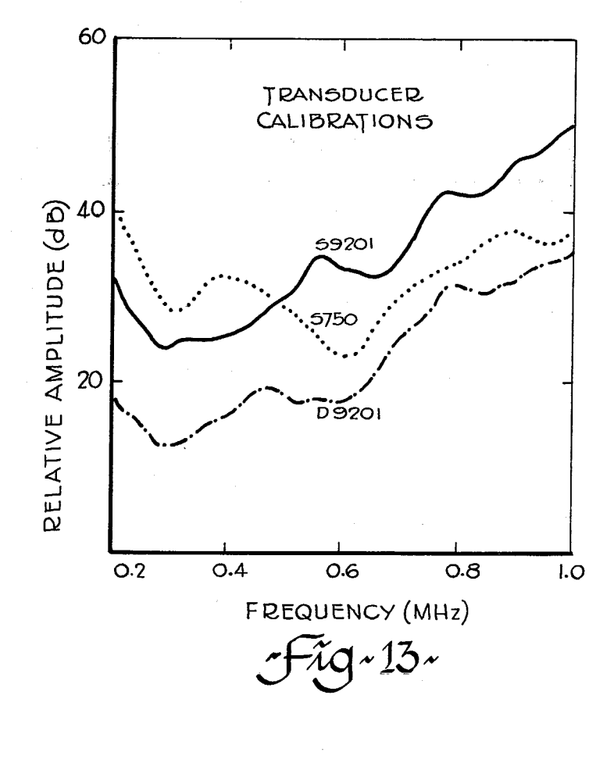
FIG. 13 is a graph showing transducer calibrations derived from the data in FIG. 12.
Figure 14:
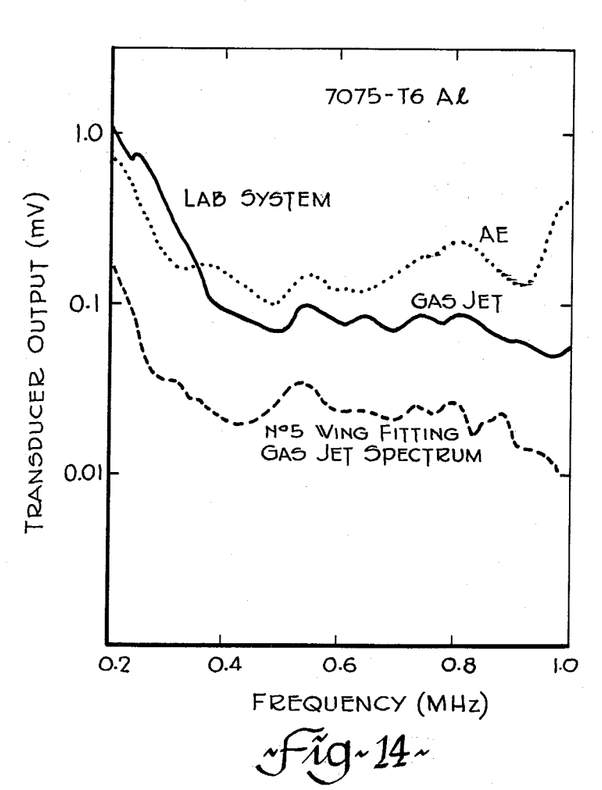
FIG. 14 is a graph correlating, by the gas jet technique, a field and laboratory system (wing fitting), also shown in an A.E. spectrum in the lab system.
Figure 15:
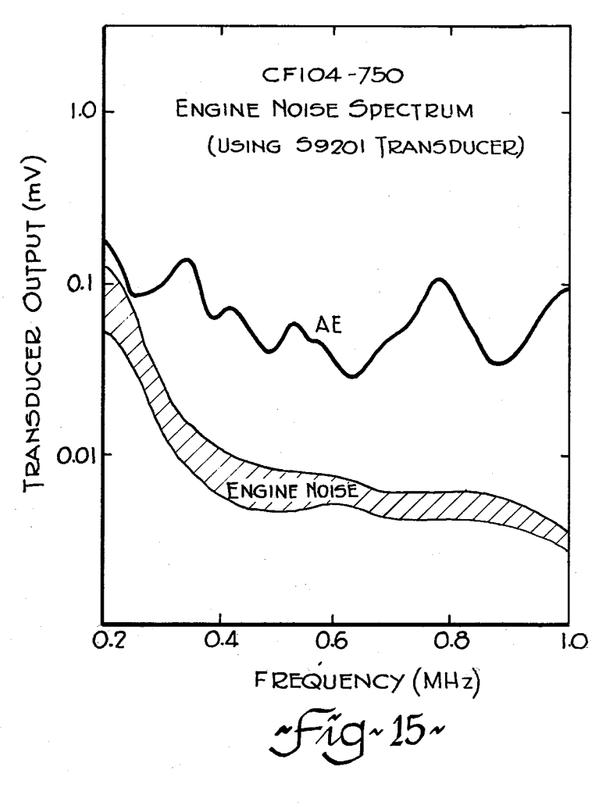
FIG. 15 is a graph showing a CF104 engine noise spectrum and the expected A.E. spectrum in the wing fitting derived from the data of FIG. 14.
Figure 16:
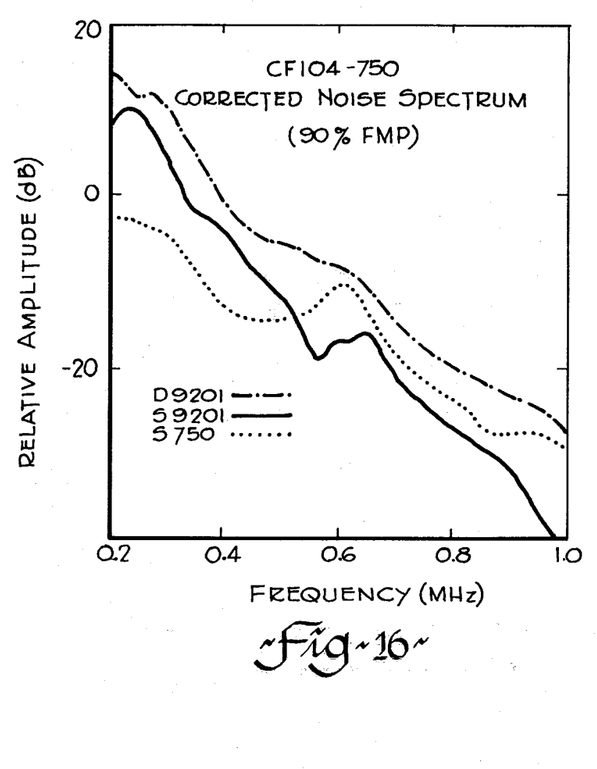
FIG. 16 is a graph showing the system corrected noise spectrum measured using several different transducers using the calibrations of FIG. 13.

In order to demonstrate the feasibility of conducting A.E. tests on large equipment in the field, the procedures outlined with reference to Example 1 were repeated using a CF104 Fighter Aircraft. After calibration of S9201, S750 and D9201 transducers as described with reference to Example 1, the transducers were attached to the number 5 wing attachment fitting and an engine noise spectrum was determined. FIG. 12 illustrates the transducer spectra ($t$ dB) obtained with the S9201, S750 and D9201 transducers using an aluminum test block and helium gas jet. The corresponding spectrum curve for the flat response quartz crystal ($q$ dB) is shown for comparison. These curves enable the transducer calibration ($t$ - $q$) dB to be made. The transducer calibrations are shown in FIG. 13. After calibration of the transducers they were coupled to the #5 wing attachment for measurement of the gas jet specimen system spectrum (s dB) as described hereinabove. As previously noted the specimen system calibration is ($s$ - $q$) dB. A.E. specimen data was collected in the laboratory specimen. The A.E. specimen spectra ($e$ dB) (as in FIG. 14) was identified and corrected to $e$ - ($s$ - $q$)dB (as in FIG. 15). These laboratory type tests enabled an understanding of the relationship between the emitting source and observed A.E. signal. The wing attachment was then tested in situ in a CF 105 Fighter Aircraft. Firstly the gas jet field system spectrum was measured (S dB), so as to determine the field system calibration (S - $q$) dB. The expected field system A.E. spectrum (uncorrected) was then deduced $E^* = e - (s - S)$ dB, from the data depicted in FIG. 14. The field system background noise spectrum NdB was then measured, as shown in FIG. 15. This enabled the expected system A.E. signal/noise ratio ($E^* - N$) dB to be deducted. On the basis of this information the most suitable transducer can be selected and a corrected noise spectrum can be derived, from the engine noise spectra, as shown in FIG. 16. It will be observed from FIGS. 15 and 16 that the A.E. signals are well above engine noise levels so that even during the running of engines it is entirely feasible to collect meaningful A.E. data of this type from a field system during service. As demonstrated herein, field system A.E. spectra (E db) can be measured by laboratory analysis and a corrected A.E. field spectrum determined E - (S - $q$) dB, so that it is possible to meaningfully compare laboratory experiments with field data. This is a necessary step to deducing material integrity, assessing probable remaining life of specific components, and even predicting failure in advance of a catastrophic failure situation, while the aircraft or other equipment is in service without the necessity of establishing the spectral response by actual destruction.

We claim:

1. A method for spectral calibration of acoustic emission systems, comprising
   a. acoustically coupling a first transducer, having a flat frequency response up to about 1 MHz, to a reference material;
   b. exciting said reference material with a broad spectrum noise means, thereby generating an output signal from said first transducer;
   c. measuring said output signal from said first transducer;
   d. acoustically coupling a second transducer to a test piece and exciting said test piece with said broad spectrum noise means, thereby generating an output signal from said second transducer;
   e. calibrating said output signal of said second transducer relative to said output signal of said first transducer;
   f. measuring an acoustic emission spectrum from said test piece; and
   g. correcting said acoustic emission spectrum relative to said calibrated output signal of said second transducer.

2. A method as claimed in claim 1 wherein said reference material and said test piece are excited by a gas jet applied to a surface thereof.

3. A method as claimed in claim 2 wherein said gas jet is a helium gas jet at 18–40 psi.

4. A method as claimed in claim 1, wherein said output signal of said first transducer, in decibels, is subtracted from the output signal of said second transducer, in decibels, thereby deriving a calibrated output of said second transducer.

5. A method as claimed in claim 4 wherein said calibrated output of said second transducer is subtracted from said acoustic emission spectrum thereby correcting said acoustic emission spectrum.

6. A method as claimed in claim 1 including the steps of:
   h. acoustically coupling said second transducer to said reference material and exciting said reference material with said broad spectrum noise means, thereby generating a second output signal from said second transducer; and
   i. calibrating said second output signal of said second transducer relative to the output signal of said first transducer.

7. A method as claimed in claim 6 wherein steps (h) and (i) are repeated for a plurality of transducers to thereby facilitate selection of a desired transducer.

8. A method for calibrating a high frequency audio transducer comprising:
   a. acoustically coupling said transducer to a reference material and exciting said material with a broad spectrum noise means comprising a gas jet applied to a surface thereof, thereby generating an output signal from said transducer;
   b. amplifying and analysing said output signal;
   c. acoustically coupling a second transducer having a flat frequency response up to about 1 MHz to said reference material excited by said broad spectrum noise thereby generating a comparison output signal from said second transducer;
   d. amplifying and analysing said comparison output signal; and
   e. calibrating said output signal against said comparison output signal.

9. A method as claimed in claim 8 wherein said gas jet is a helium gas jet applied at 18–40 psi.

10. Apparatus for use in spectral calibration of acoustic emission systems comprising:
    a reference material;
    a test piece;
    broad spectrum noise means for excitation of said reference material and said test piece;
    transducer means for acoustic coupling to said test piece;
    a comparison transducer having a flat frequency response up to about 1 MHz for acoustic coupling to said reference material; and
    means for recording and analysing an output signal from said transducer means coupled to said test piece relative to an output signal from said comparison transducer coupled to said reference material to produce a calibrated output signal representative of an acoustic emission event in said test piece.

11. Apparatus as claimed in claim 10 wherein said noise means is a gas jet.

12. Apparatus as claimed in claim 11 wherein said gas jet is a helium gas jet.

13. Apparatus as claimed in claim 10, wherein said reference material is an aluminum block.

14. Apparatus as claimed in claim 10, wherein said comparison transducer is an X-cut quartz crystal having a fundamental mechanical resonance at about 5 MHz.

15. Apparatus as claimed in claim 10, including means to amplify, filter and analyse output signals from said transducer means and said comparison transducer.

* * * * *